United States Patent
Mendoza

(10) Patent No.: US 6,689,571 B1
(45) Date of Patent: Feb. 10, 2004

(54) ASSAY METHOD AND KIT FOR PYTHIUM INSIDIOSUM ANTIBODIES

(75) Inventor: Alberto Leonel Mendoza, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/293,731

(22) Filed: Nov. 13, 2002

(51) Int. Cl.[7] ............... G01N 33/53; G01N 33/546; G01N 33/544; G01N 33/543
(52) U.S. Cl. ............... 435/7.31; 435/7.1; 435/7.2; 435/180; 436/533; 436/528; 436/518
(58) Field of Search ............... 435/7.2, 7.1, 7.31, 435/180; 436/518, 533, 528

(56) References Cited

U.S. PATENT DOCUMENTS

| 4,829,012 A | 5/1989 | Cambiaso et al. ........... 436/512 |
| 5,290,517 A | 3/1994 | Samuels et al. ............... 422/58 |
| 5,534,441 A | 7/1996 | Miyazaki et al. ........... 436/517 |
| 5,652,149 A | 7/1997 | Mileaf et al. ................ 436/518 |
| 5,795,719 A | 8/1998 | Richard et al. ................. 435/6 |
| 5,948,413 A | 9/1999 | Mendoza .................. 424/274.1 |
| 6,287,573 B1 | 9/2001 | Mendoza .................. 424/434.1 |

OTHER PUBLICATIONS

Rinaldi, M.G., et al., Mycology Observer 9:7 (1989).
Mendoza, L., et al., Clin. Diagnost. Lab. Immunol. 4: 715–718 (1997).
Mendoza, L., et al., J. Clin. Microbiol. 23: 813–816 (1986).
Palmer et al, Serodiagnosis of Mycotic Diseases. American Lecture Series. Thomas, Springfield, IL. USA pp. 131–139 (1977).

Primary Examiner—S. Devi
(74) Attorney, Agent, or Firm—Ian C. McLeod

(57) ABSTRACT

A method and test kit for an agglutination assay for antibodies in human or other mammal serum is described. The kit preferably contains latex particles and uses extracellular antigen(s) of *Pythiosis insidiosum* which bind to the particles and which in turn bind to the serum antibodies to produce the agglutination. The assay is particularly important for detecting early stages of Pythiosis.

**

ASSAY METHOD AND KIT FOR PYTHIUM INSIDIOSUM ANTIBODIES

BACKGROUND OF THE INVENTION (1) Field of the Invention

The present invention relates to a particle agglutination assay for *Pythium insidiosum* antibodies in a serum sample. In particular, the present invention uses antigens from *Pythium insidiosum* with the latex particles, wherein the particles are agglutinated in the presence of the serum antibody or antibodies. The result is the rapid detection of *Pythium insidiosum* antibodies in a sample serum, usually in five (5) minutes or less.

(2) Description of Related Art

Infections caused by fungal and parafungal organisms are occurring with increasing frequency in patients with debilitating illnesses such as leukemia and AIDS, as well as those undergoing immunosuppressive therapy. Within this group of organisms are the traditional pathogenic fungi and a long list of newly recognized emerging opportunistic fungal and parafungal organisms. Among the emerging pathogens is the oomycete *Pythium insidiosum*, a fungal-like organism in the Kingdom Kromista, Phylum Pseudofungi. *Pythium insidiosum* is not only physiologically distinct from members of the Kingdom Fungi, but also phylogenetically. This may explain why anti-fungal drugs do not have any effect on pythiosis.

*Pythiosis insidiosi* particularly occurs in humans and lower animals in the tropical, subtropical, and temperate areas of the world (Cock, W. A. W., et al., J. Clin. Microbiol. 25:344–349 (1987)). The disease was described in the beginning of the $20^{th}$ century in equines of tropical and subtropical countries including India and Indonesia as well as the USA. Soon, however, it was evident that the disease not only affected equines but other mammalian species as well. In lower animals infections of the cutaneous tissues, lymphatic vessels, intestines, lungs, and bones have been found. In humans, a deadly arteritis infection, subcutaneous invasion and keratitis occurs.

Thus, *Pythium insidiosum* is a protist that causes infection in mammals, most often horses and dogs, but sometimes humans. It enters the body through wounds or the GI tract from contaminated plants, soil or water. It causes granulomatous lesions to form wherever it gains a foothold in the body, and can spread to other sites via the lymphatic system. It is 100% fatal if not treated. Early diagnosis greatly increases the chances for survival of the host, as treatment becomes less effective the longer the infection progresses.

The currently available drugs used to treat fungal infections have had little or no effect on *Pythium insidiosum*. Reports of treatment with either amphotericin B or surgery, commonly used to treat this disease in both humans and lower animals, have indicated that 60% of the patients died of their infections. In cases of arterial invasion in humans, amphotericin B did not eliminate the infection (Rinaldi, M. G., et al., Mycology Observer 9:7 (1989); and Thianprasit, M., Trop Dermathol 4:1–4 (1990)), whereas in surgery the main problem has been to determine how much of the infected tissues has to be removed. Thus, relapses are common in surgically treated patients, who must also endure the pain and distress that such an invasive traumatic procedure inflicts on them.

My U.S. Pat. Nos. 5,948,413 and 6,287,573, which are incorporated herein by reference, describes very effective vaccines of *Pythiosis insidiosi* proteins for the treatment of Pythiosis. The problem has been to identify the disease at an early enough stage so that the vaccine can be maximally effective.

Various immunodiffusion (ID) and enzyme linked immunoabsorbant assays (ELISA) have been developed to detect *Pythiosis insidiosum* but they are more expensive and less reliable because of cross-reactivity of the antibodies (Grooters, A.M., et al., J. Vet. Intern. Med. 16:142–146 (2002); Imwidthaya, P., et al., Mycopathologia 106:109–112 (1989); Mendoza, L., et al., Clin. Diagnost. Lab. Immunol. 4:715–718 (1997); and Mendoza, L., et al., J. Clin. Microbiol. 23:813–816 (1986)). The main problem has been that these tests have to be performed by qualified laboratories and professionals. All of the currently available diagnostic tests require specialized knowledge and equipment, and there are only two laboratories in the U.S. that are equipped to perform them. A clinician who suspects pythiosis must send a serum or tissue sample to one of these two laboratories to be tested, which delay the beginning of treatment.

Latex agglutination assay methods and kits for testing for mammalian animal and human fungal pathogens are well known. One reference dealing with such methods is Serodiagnosis of Mycotic Diseases, American Lecture Series. Thomas, Springfield, Ill., USA pp 131–139 (1977) by Palmer, D. F., et al. There has been no suggestion of the use of this type of assay for *Pythiosis insidiosi*.

OBJECTS

It is therefore an object of the present invention to provide an agglutination assay and test kit for *Pythium insidiosum* antibodies in serum sample.

It is further an object of the present invention to provide an assay and test kit which is rapid and reliable so as to be performable in the field or at the bedside of the patient.

These and other objects will become increasingly apparent by reference to the following description and drawings.

SUMMARY OF THE INVENTION

The present invention relates to a particle agglutination assay kit for detecting *Pythium insidiosum* antibodies in a serum sample which comprises:

(a) at least one *Pythium insidiosum* antigen which is unique to *Pythium insidiosum* and complexes with *Pythium insidiosum* antibodies which can be present in a serum sample;

(b) particles which complex with the *Pythium insidiosum* antigen;

(c) a negative control serum which is free of *Pythium insidiosum* antibodies;

(d) a positive control serum which contains *Pythium insidiosum* antibodies; and (e) at least one device for separately mixing the antigen and the particles with (1) the serum sample; (2) the positive control serum, and (3) the negative control serum, wherein if the serum sample contains the *Pythium insidiosum* antibodies which complex with the antigen, the particles are agglutinated and are compared to the positive and negative control serums. Preferably there are multiple of the antigens which are expressed from cells of the *Pythium insidiosum* in a culture medium and then isolated and purified from the culture medium.

In particular the present invention relates to a method for assaying for *Pythium insidiosum* antibodies in a serum sample which comprises:

(a) providing:
  (1) at least one *Pythium insidiosum* antigen which is unique to *Pythium insidiosum* and complexes with *Pythium insidiosum* antibodies which can be present in a serum sample;
  (2) particles which complex with the *Pythium insidiosum* antigen;
  (3) a negative control serum which is free of *Pythium insidiosum* antibodies;
  (4) a positive control serum which contains *Pythium insidiosum* antibodies; and
  (5) at least one device for separately mixing the antigen and the particles with (1) the serum sample; (2) the positive control serum, and (3) the negative control serum, wherein in the assay if the serum sample contains the *Pythium insidiosum* antibodies which complex with the antigen, the particles are agglutinated and are compared to the positive and negative control serums; and
(b) testing the serum sample, negative and positive controls with the particles and the antigen to determine if there is agglutination of the latex particles by the sample serum. The method can be used for the testing on human serum or animal serum. Preferably the testing is of horse serum. Preferably the particles are latex. The incorporated prior art describes numerous types of particles which can be used.

DESCRIPTION OF PREFERRED EMBODIMENTS

Figure 1:
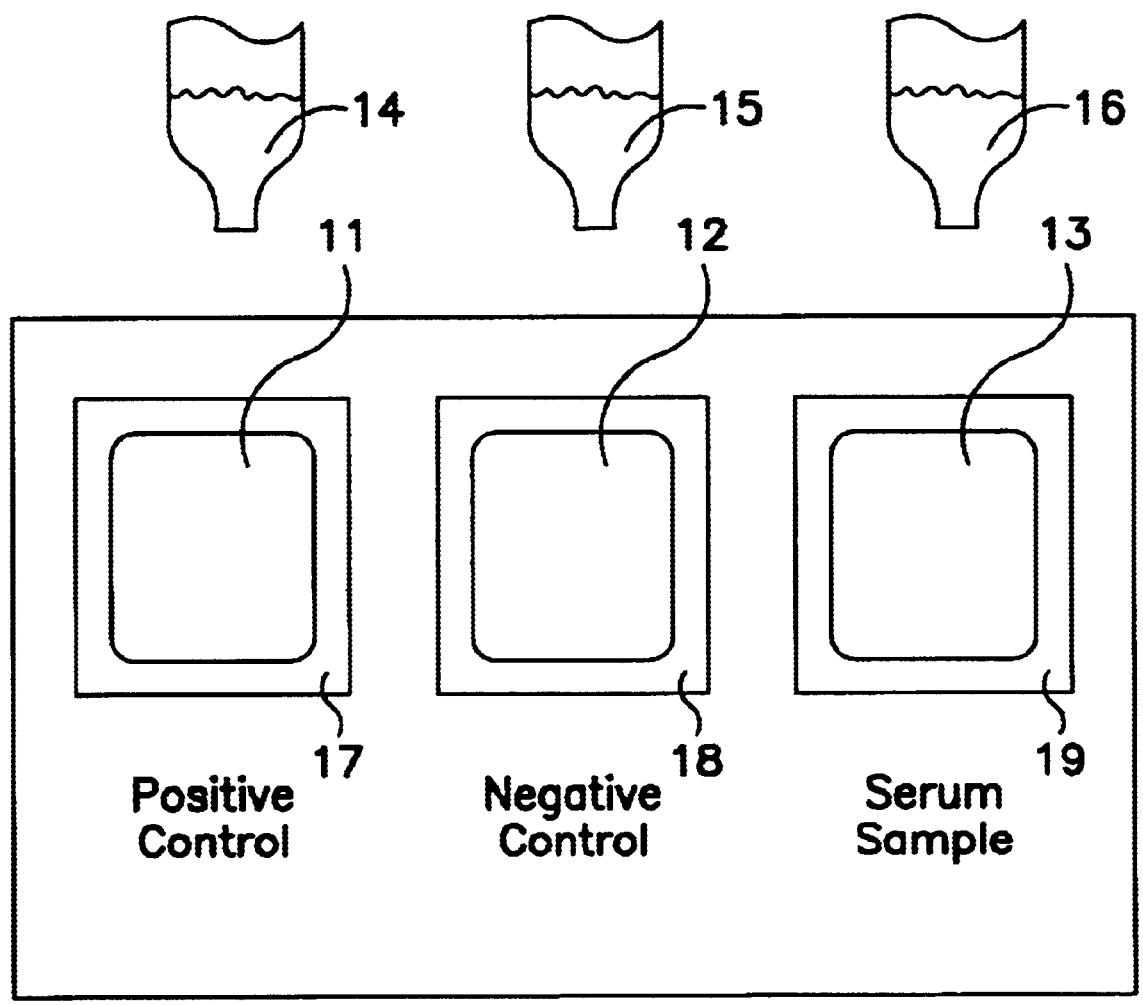
FIG. 1 is a schematic view of micropipettes 14, 15 and 16 delivering an aliquot to inner surfaces 11, 12 and 13 of a test strip bounded by rings 17, 18 and 19. The surfaces 11, 12 and 13 are dark colored so as to be in contrast to the lighter colored particles.

In particular, a latex agglutination test was developed to detect anti-*P. Insidiosum* antibodies in animals and humans. This test proved to be very sensitive and specific. The development of a *P. insidiosum*-latex agglutination test allows clinicians to do early diagnosis in their clinical settings, thus shortening the time between diagnosis and treatment.

U.S. Pat. Nos. 5,795,719, 5,652,149, 5,290,517, 5,534,441 and 4,829,012, which are incorporated by reference, describe various types of agglutination assays using particles which agglutinate as a result of an antigen reaction with antibodies in serum. The assays can be a simple visual assay or can employ optical means. Typically the particles are modified to bind to the antigen which can be by chemical or physical means generally referred to herein as "complex". All of this terminology is well known to those skilled in the art.

The preferred polystyrene latex particles are commonly available from Latex Beads, Sigma Chemicals, St. Louis, Mo. The particles generally have dimensions between about 0.8 and 0.9 microns. Test strips used are available from multiple sources.

The antigens were preferably obtained from those expressed into a growth medium extracellularly of the *Pythium insidiosum*. The antigens are described in U.S. Pat. Nos. 5,948,413 and 6,287,573, referred to above. The dominant antigens are 30–33 Kd in size as measured by gel electrophoresis.

*Pythium insidiosum* was deposited with the American Type Culture Collection under the Budapest Treaty as ATCC 74446 in the above U.S. patents. It was also deposited as ATCC 58643. It is available upon request by name and number. All restrictions on distribution of ATCC 74446 have been irrevocably removed. The address of the American Type Culture Collection is 10801 University Blvd. Manassas, Va. 20110-2209.

The proteins used in the method and kit of the present invention are isolated by (a) growing cells of *Pythium insidiosum* in a broth culture medium; (b) separating the cells from a supernatant of the culture medium which contains extracellular proteins; separating the combined proteins from the supernatant; mixing the separated proteins in sterile distilled water; and concentrating the proteins to remove low molecular weight components less than 10,000 MW.

The intracellular proteins can be produced in the same manner by killing the cells; disrupting the cells in sterile water; separating the disrupted cells from the water to produce a supernatant containing intracellular proteins. The intracellular and extracellular (expressed) proteins can be mixed together, although, because the antibodies in the serum are dominantly expressed as a result of exogens, it is preferred to use only the extracellular proteins.

The antigen was prepared as per Mendoza et al (Clin. Diagnost. Lab. Immunol. 4:715–718 (1997)). Briefly, the ATCC 58643 type strain of *P. insidiosum* was cultured in 500 ml Sabouraud broth. The supernatant was collected and concentrated 100× in a stir cell (Amicon). The reactivity of this antigen was confirmed by immunodiffusion and kept at 4° C. until use. The optimal proportions of polystyrene latex (0.8 $\mu$m, Sigma), antigen solution, and serum (from a high titer pythiosis case positive in ELISA and culture) were determined according to Palmer et al (Serodiagnosis of Mycotic Diseases American Lecture Series. Thomas, Springfield, Ill., USA. Pp. 131–139 (1977)). In summary, the 100× concentrated antigen was serially diluted, and each dilution mixed with a constant concentration of latex. After incubation at room temperature for 15 minutes, each antigen-latex mixture was reacted with each of a series of dilutions of positive and negative control sera. The dilution that gave ++++ reaction with the positive control serum was selected as the working dilution. Once the optimum concentration of reactant was found, the sensitivity and specificity of the test was evaluated using 158 homologous, heterologous and sera from apparently healthy humans and animals. All sera were inactivated at 55° C. for 30 minutes previous to the test.

EXAMPLE 1

Preparation of extracelluar antigens (proteins):

1. The antigen was prepared as per Mendoza et al (Clin. Diagnost. Lab. Immunol. 4:715–718 (1997)). *Pythium insidiosum* strain ATCC 58643 (also known as ATCC 74946), was transferred to a 1.0-liter flask containing 500 ml of Sabouraud dextrose broth (Difco, Sparks, Md.).

2. Cultures were incubated at 37° C. for five days on shaker rotating at 150 rpm.

3. Cultures were killed with Merthiolet (thimersol) (0.02% wt/vol,), filtered to separate the cells (hyphae) from the liquid phase containing exoantigens of *P. insidiosum*.

4. The proteins were then precipitated with an equal volume of acetone and pelleted at 20,000×g for 30 minutes in a refrigerated centrifuge.

5. The pellet was resuspended in sterile distilled water at ~2.0 mg/ml protein concentration.

6. The mixture was concentrated in a 100× stir cell (Amicon, Bedford, Mass.). The reaction of the antigen mixture confirmed by microdiffusion and kept at 4° C. until use.

EXAMPLE 2

The optimal proportions of polystyrene latex (0. 8 μm, Sigma), antigen solution, and serum (from a high titer pythiosis case positive in ELISA and culture) were determined according to Palmer et al (Palmer, D. F., et al., Serodiagnosis of Mycotic Diseases. American Lecture Series. Thomas, Springfield, Ill., USA. Pp. 131–139 (1977)). In summary, the 100× concentrated antigen was serially diluted, and each dilution mixed with a constant concentration of latex. After incubation at room temperature for 15 minutes, each antigen-latex mixture was reacted with each of a series of dilutions of positive and negative control sera. The dilution that gave ++++ reaction with the positive control serum was selected as the working dilution. Once the optimum concentration of reactants was found, the sensitivity and specificity of the test was evaluated using 158 homologous, heterologous and sera from apparently healthy humans and animals. All sera were inactivated at 55° C. for 30 minutes previous to the test.

Determination of Optimum Latex: Antigen Ratio in Slide Latex Agglutination Test for Pythiosis: Materials and Methods I. Materials and Reagents
  A. Glycine buffered saline (GBS), pH 8.4.
    1. Glycine
    2. NaCl
    3. 1N NaOH
  B. Glycine buffered saline-0.1% bovine serum albumin (GBS-BSA)
    1. GBS, pH 8.4
    2. Bovine Serum Albumin
  C. Sterilized, deionized water
  D. 0.81μ polystyrene latex particle suspension, (Sigma, Lot 11K0085), diluted with GBS; 1 mL latex in 1.75 ml total volume.
  E. *Pythium insidiosum* culture filtrate antigen (exoantigens).
  F. Heat-inactivated sera:
    1. Positive control serum #14 (proven positive for infection by Pythium by culture, histology, and serology.)
    2. Negative control serum from a human, proven negative by immunodiffusion.
  G. 1.5-ml microcentrifuge tubes
  H. 3 spatulas
  I. 125 ml Erlenmeyer flask
  J. 50 ml Erlenmeyer flask
  K. 50 ml volumetric flask w/glass stopper
  L. 25 ml volumetric flask w/glass stopper
  M. Magnetic plate/stir bar
  N. Rotary shaker
  O. pH meter
  P. Microfuge tube racks
  Q. Automatic micropipettes and tips (p20, p200, p1000)
  R. Wooden applicator sticks
  S. Plastic cards with black background (from commercial latex agglutination kit, Biokit, S.A., Barcelona, Spain)

II. Preparation of Reagents
  A. Autoclave the following:
    1. Two hundred ml deionized water
    2. Two Erlenmeyer flasks (125 and 50 ml)
    3. Two volumetric flasks (50 and 25 ml)
    4. Two glass stoppers for the volumetric flasks
    5. 3 spatulas
    6. Pipette tips
    7. 1.5-ml microfuge tubes
  B. Glycine Buffered Saline (GBS), pH 8.4. Chemicals needed: NaCl, Glycine, 1N NaOH, distilled water.
    1. Add approximately 40 ml deionized, sterilized water to the 125-ml Erlenmeyer flask.
    2. Using a magnetic stir bar and stir plate, dissolve 0.450 g NaCl in the distilled water.
    3. Add 0.375 g glycine and mix to dissolve
    4. Transfer the solution to the 50 ml volumetric flask, rinsing the Erlenmeyer flask with sterile water. Add sterilized, distilled water q.s. to 50 ml and mix thoroughly.
    5. Transfer the solution back into the Erlenmeyer flask. Check the pH with a prestandardized pH meter. Add sufficient 1N NaOH to bring the pH of the solution to 8.4+/−0.05
    6. This buffer should be used the same day it is made.
  C. GBS-0.1% Bovine Serum Albumin (GBS-BSA), pH 8.4. Chemicals needed: GBS, pH 8.4, Bovine serum albumin (Fraction V).
    1. Add about 20 ml GBS, pH 8.4 to 50 ml Erlenmeyer flask.
    2. Using a stir bar and magnetic plate, dissolve 0.025 g bovine serum albumin in the GBS.
    3. Transfer the solution to a 25 ml volumetric flask, rinsing the Erlenmeyer flask with GBS, and adding the rinse to the volumetric flask. Add GBS q.s. to 25 ml and mix again.
    4. Use the same day.

III. Block Titration for Determining Optimal Sensitization of the Latex Suspension
  A. Label 7 sterile microcentrifuge tubes #1–7.
  B. Fill the tubes in the following manner:

TABLE 1

| Tube # | μL GBS | μL Antigen | μL stand. Latex |
|---|---|---|---|
| 1 | — | 100 | 100 |
| 2 | 50 | 50 | 100 |
| 3 | 150 | 50 | 200 |
|  |  | μL Antigen + latex |  |
| 4 | 200 | 200 from Tube 3 | — |
| 5 | 200 | 200 from Tube 4 | — |
| 6 | 200 | 200 from Tube 5 | — |
| 7 | 50 | — | 50 |

Mix the contents of each tube before transferring any to the next. Make sure latex is well mixed; shake it for a count of 60 before pipetting any out.
  C. Make sure all tubes have been well mixed; incubate at room temperature for at least 15 minutes.
  D. Make serum dilutions:
    1. Label a set of 4 1.5 ml microfuge tubes S+und., S+1:2, S+1:4, and S+1:8.
    2. Add 400 μL GBS-BSA to the second through the fourth tubes (S+1:2 through S+1:8).
    3. Add 800 μL of the heat-inactivated positive control serum to the first tube (S+und.).

4. Transfer 400 μL of the serum from the first to the second (S+1:2) tube, which contains 400 μL GBS-BSA. Mix by pipetting up and down, or flicking. Without changing pipette tips, transfer 400 μL of the contents of the second tube to the third tube (S+1:4). Mix, and transfer 400 μL from the third to the fourth (S+1:8) tube.
5. Repeat steps 1–4, labeling the tubes "S–" instead of "S+", and using the negative control serum.

E. Perform test:
1. Pipet 20 μL of the latex-antigen mixture from Tube 6 onto the sixth space on the reaction card from the commercial kit. Pipet 20 μL from Tube 5 onto the fifth space, 20 μL from Tube 4 onto the fourth space, and so on through Tube 1. The pipette tips need not be changed between tubes if they are done in order of least to most diluted latex-antigen mix.
2. Pipet 40 μL of the undiluted negative control latex onto each of the drops of latex-antigen mix on the card, changing pipette tips between drops.
3. With applicator sticks (a clean end for each drop) mix together each drop of serum-latex-antigen, spreading each one into a smooth oval that fills most of the marked space on the card. Place on a rotary shaker set at 100–150 rpm. Wait 15–20 min for the reaction to develop.
4. Repeat steps 1–3, using a different serum dilution for all the spaces on each card, until all the positive and negative sera have been tested. Record results. For a "4+" reaction: clumps of latex form and all form a ring around the edge of the droplet. For a "3+" reaction: lots of large latex clumps, but they don't form a ring. A "2+" reaction: clumps clearly visible, but not as heavy as a "3+." For a "+", clumps of latex small and hard to see, need magnifying glass to see clearly.
5. Pipet 20 μL of the "latex only" dilution from Tube 7 onto each of four spaces on a card. Pipet 40 μL of the undiluted positive control serum onto the first droplet of latex. Change pipette tips; pipet 40 μL of the 1:2 pos. serum dilution (S+1:2) onto the second drop, and so on for the rest of the dilutions of the positive control serum. Mix with applicator sticks, place on rotary shaker for 15–20 minutes. Record results.

EXAMPLE 3

A total of 158 sera were tested using the new *P. insidiosum* latex agglutination test. Some of these sera were previously used to evaluate the sensitivity and specificity of both an ELISA and an ID *P. insidiosum* assays (Mendoza, L. et al., Clin. Diagnost. Lab. Immunol. 4:715–718 (1997)). These are the sera used in this study: a) Sixty-one sera from apparently healthy humans (n=23), horses (n=16), dogs (n=17), and cats (n=5), were used as negative controls; b) nineteen sera from humans and animals with proven pythiosis; c) thirty sera from horses and dogs clinically suspected of pythiosis, but negative in ID and ELISA; and d) nineteen sera from human and animals with heterologous diseases such as aspergillosis (n=3), basidiobolomycosis (n=2), blastomycosis (n=1), coccioidomycosis (n=3), conidiobolomycosis (n=6), histoplasmosis (n=3), and cryptococcosis (n=1).

The latex agglutination test was negative in all human and animal sera used as controls and it did not cross-react with any of the heterologous diseases sera, proving its specificity (Table 2). When it was tested with sera from suspected cases of pythiosis that were previously considered negative in the ELISA and the ID tests, the latex agglutination test gave negative results confirming again its specificity. From 48 sera of humans and animals with proven pythiosis tested in the latex agglutination test, 42 gave 4+ to 1+ positive reactions. The six sera negative in the latex agglutination test were all positive, but with very low titer in ELISA and negative in ID (Table 2).

The results indicated that the latex agglutination test possess high specificity (100%) and an adequate sensitivity (87.5%) to detect cases of pythiosis in both humans and animals (Table 3). It is definitely more sensitive than the ID test which detected only 30 cases of proven pythiosis out of 48 sera tested (62.5%). The ELISA test continues to be the most sensitive test for pythiosis, but it has a disadvantage. It can only be performed by specialized laboratories and it takes several days for the results. In contrast, the new simplified latex agglutination test can be performed in the clinical setting and only takes 5 minutes for the results. We believe that the latex agglutination test could be of great help for clinicians working in endemic areas of pythiosis, especially those dealing with patients suspected of intestinal pythiosis.

TABLE 2

|  | Controls | Pythiosis* | Heterologous Diseases | Suspected ¶ Pythiosis |
|---|---|---|---|---|
| Latex | Neg. | 42+ | Neg. | Neg. |
| ELISA | Neg. | 33+ | Neg. | Neg. |
| ID | Neg. | 30+ | Neg. | Neg. |
| Total tested | n = 61 | n = 48 | n = 19 | n = 30 |

*Cases of pythiosis confirmed by serology, culture, and/or histopathology.
¶Clinically suspected cases of pythiosis, but negative in ID or ELISA.

When the test was of sera from suspected cases of pythiosis that were previously considered negative in the ELISA and the ID tests, the latex agglutination test gave negative results confirming its specificity. From 48 sera of humans and animals with proven pythiosis tested in the latex agglutination test, 42 gave 4+ to 1+ positive reactions. The six sera negative in the latex agglutination test were all positive with very low titer in ELISA (Table 2).

The results indicated that the latex agglutination test possesses high specificity (100%) and an adequate sensitivity (87.5%) to detect cases of pythiosis in both humans and animals (Table 3).

TABLE 3

|  | LATEX | | | ELISA | | | ID | | |
|---|---|---|---|---|---|---|---|---|---|
| Controls n = 50 | 61 | none | 61 | 36 | none | 36 | 43 | none | 43 |
| pythiosis n = 48 | 48 | 42 | 6* | 33 | 33+ | none | 48 | 30 | 18 |
| Hete. Dis. N = 19 | 19 | none | 19 | 18 | none | 18 | 19 | none | 19 |

●These sera reacted positive in ELISA
+Including six sera that reacted negative in the latex agglutination test
P = Positive
N = Negative The test of the present invention is definitely more sensitive than the ID test which detected only 30 cases of proven pythiosis out of 48 sera tested (62.5%). The ELISA test continues to be the most sensitive test for pythiosis, but it has a disadvantage present also in the western blot. It can only be performed by specialized laboratories and it takes several days for the results. In contrast, the new latex agglutination test can be performed in the clinical setting and only takes 5 minutes for the results. The latex agglutination test is of great help for clinicians working in endemic areas of pythiosis, especially those dealing with patients that suspect intestinal pythiosis.

It is intended that the foregoing description be only illustrative of the present invention and that the present invention be limited only by the hereinafter appended claims.

I claim:

1. A method for assaying for *Pythium insidiosum* antibodies in a serum sample which comprises:
   (a) providing:
      (1) isolated *Pythium insidiosum* antigens comprising dominant 30–33 Kd extracellular proteins which complex with *Pythium insidiosum* antibodies that can be present in a serum sample;
      (2) particles which complex with the *Pythium insidiosum* antigens;
      (3) a negative control serum which is free of *Pythium insidiosum* antibodies;
      (4) a positive control serum which contains *Pythium insidiosum* antibodies; and
      (5) at least one device for separately mixing the antigen and the particles with (1) the serum sample; (2) the positive control serum, and (3) the negative control serum, wherein in the assay if the serum sample contains the *Pythium insidiosum* antibodies which complex with the antigen, the particles are agglutinated and are compared to the positive and negative control serums; and
   (b) testing the serum sample along with negative and positive controls with the particles and the antigens to determine if there is agglutination of the particles by the sample serum.

2. The method of claim 1 which uses the antigens which are expressed from cells of *Pythium insidiosum* and then isolated and purified from a culture medium containing the cells.

3. The method of claims 1 or 2 wherein the serum sample tested is human serum.

4. The method of claims 1 or 2 wherein the serum sample tested is animal serum.

5. The method of claims 1 or 2 wherein the testing on the serum sample tested is horse serum.

6. The method of claims 1 or 2 wherein the particles are polystyrene latex.

7. The method of claim 1 wherein the antigens are a mixture of extracellular proteins comprising the dominant 30–33 Kd extracellular proteins.

* * * * *